(12) United States Patent
Zucchelli

(10) Patent No.: US 11,491,278 B2
(45) Date of Patent: Nov. 8, 2022

(54) CAP HUB INTERFACE FOR INTRADERMAL INJECTION DEVICE

(71) Applicant: Becton Dickinson France, Le Pont de Claix (FR)

(72) Inventor: Jeremy Zucchelli, Saint martin d'Heres (FR)

(73) Assignee: Becton Dickinson France, Le Pont de Claix (FR)

( * ) Notice: Subject to any disclaimer, the term of this patent is extended or adjusted under 35 U.S.C. 154(b) by 548 days.

(21) Appl. No.: 16/614,467

(22) PCT Filed: Jun. 1, 2018

(86) PCT No.: PCT/IB2018/000675
§ 371 (c)(1),
(2) Date: Nov. 18, 2019

(87) PCT Pub. No.: WO2018/220441
PCT Pub. Date: Dec. 6, 2018

(65) Prior Publication Data
US 2020/0171245 A1 Jun. 4, 2020

Related U.S. Application Data

(60) Provisional application No. 62/513,740, filed on Jun. 1, 2017.

(51) Int. Cl.
*A61M 5/00* (2006.01)
*A61M 5/31* (2006.01)
(Continued)

(52) U.S. Cl.
CPC .......... *A61M 5/3134* (2013.01); *A61M 5/345* (2013.01); *A61M 5/3293* (2013.01);
(Continued)

(58) Field of Classification Search
CPC .. A61M 2005/2444; A61M 2005/3104; A61M 39/1011; A61M 5/3134;
(Continued)

(56) References Cited

U.S. PATENT DOCUMENTS 5,624,402 A 4/1997 Imbert
8,465,461 B2 6/2013 Wu et al.
(Continued)

FOREIGN PATENT DOCUMENTS

GB 2444278 A 6/2008
JP 200843388 A 2/2008
(Continued)

*Primary Examiner* — Rebecca E Eisenberg
(74) *Attorney, Agent, or Firm* — The Webb Law Firm

(57) ABSTRACT

An injection device including a syringe including a barrel having a distal end and a proximal end and a tip provided on the distal end of the barrel, the barrel defining an internal bore extending from the proximal end to the distal end of the barrel; a luer lock adaptor including a body having a proximal end and a distal end, a reduced-diameter portion provided on the proximal end of the body, and a threading provided on an outer surface of the body, the reduced-diameter portion defining an opening to receive the tip of the syringe in a friction fit; and a needle hub including a body defining an inner cavity, a needle receiving portion extending distally from the body, and a skirt extending inwardly into the inner cavity.

12 Claims, 7 Drawing Sheets

(51) Int. Cl.
    *A61M 5/34*    (2006.01)
    *A61M 5/32*    (2006.01)
    *A61M 39/10*   (2006.01)
    *A61M 5/24*    (2006.01)
(52) U.S. Cl.
    CPC ......... *A61M 5/343* (2013.01); *A61M 39/1011* (2013.01); *A61M 2005/2444* (2013.01); *A61M 2005/3104* (2013.01)
(58) Field of Classification Search
    CPC .... A61M 5/3293; A61M 5/343; A61M 5/345; A61M 2039/1094; A61M 39/10
    See application file for complete search history.

(56)  References Cited

U.S. PATENT DOCUMENTS

| | | |
|---|---|---|
| 9,764,098 B2 | 9/2017 | Hund et al. |
| 2002/0010433 A1 | 1/2002 | Johnson et al. |
| 2015/0246184 A1 | 9/2015 | Hund et al. |
| 2016/0022925 A1 | 1/2016 | Zenker |
| 2016/0095978 A1 | 4/2016 | Iwase |
| 2017/0014310 A1* | 1/2017 | Hyun .................. A61J 15/0026 |

FOREIGN PATENT DOCUMENTS

| | | |
|---|---|---|
| JP | 201356009 A | 3/2013 |
| JP | 2015155020 A | 8/2015 |
| JP | 2016501061 A | 1/2016 |

* cited by examiner

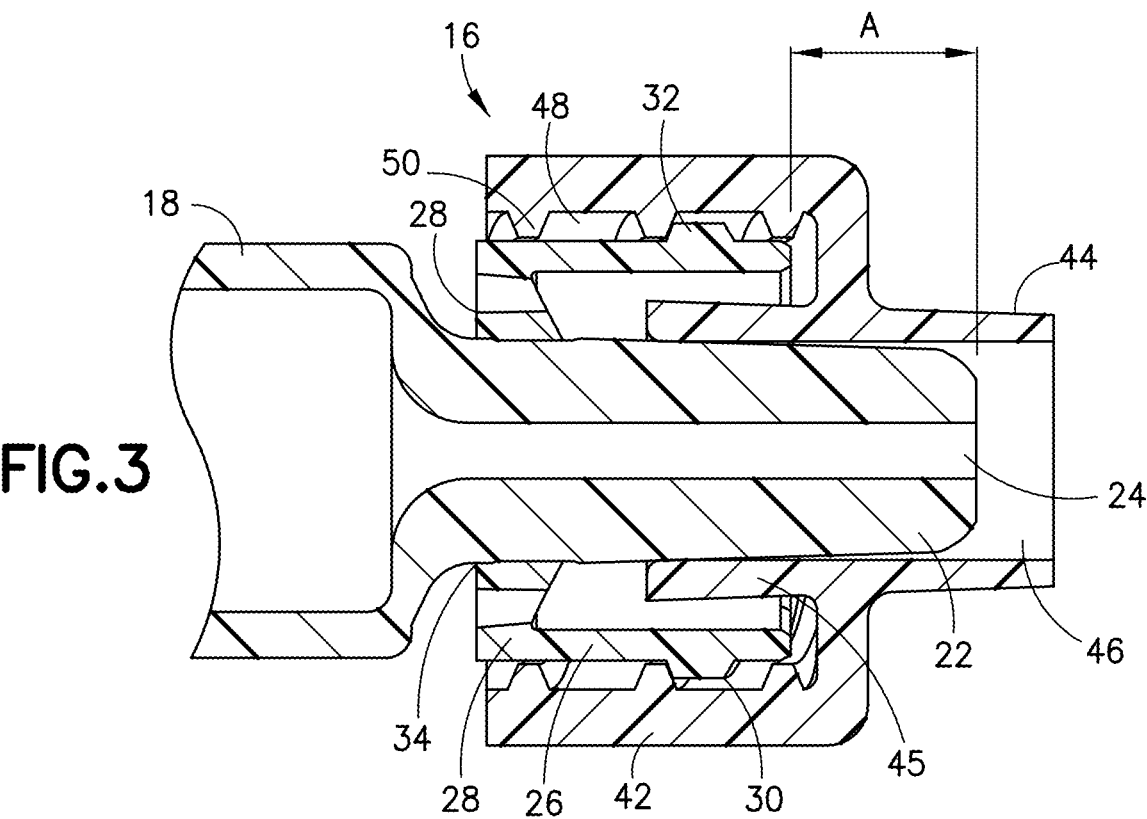
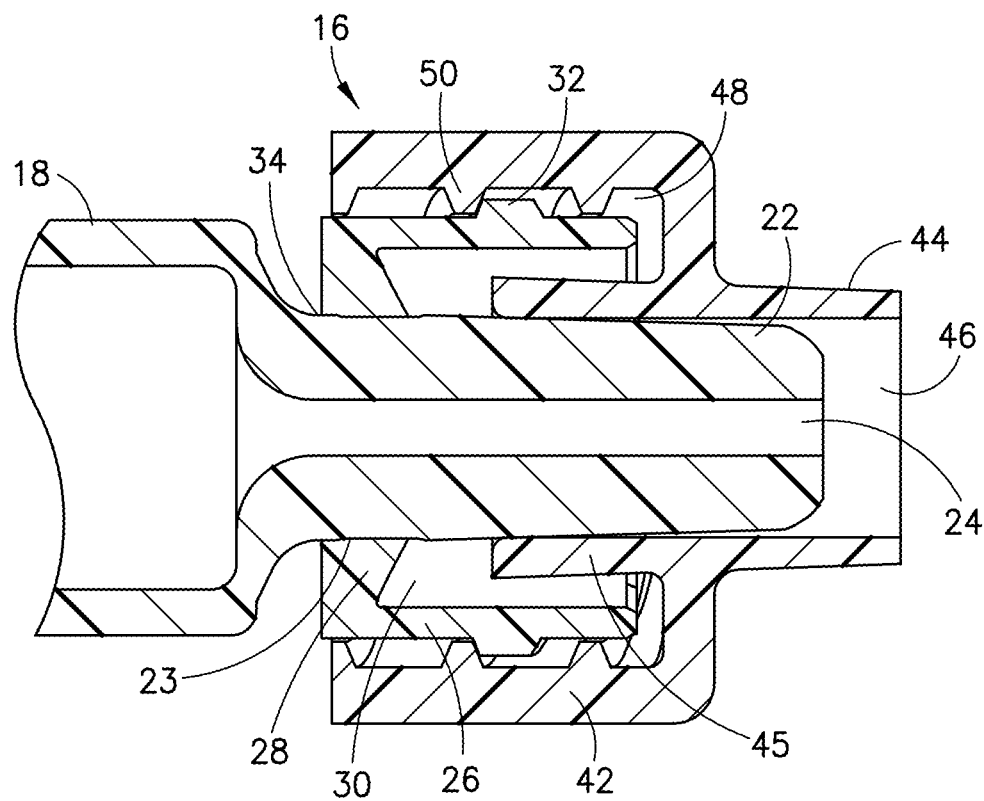

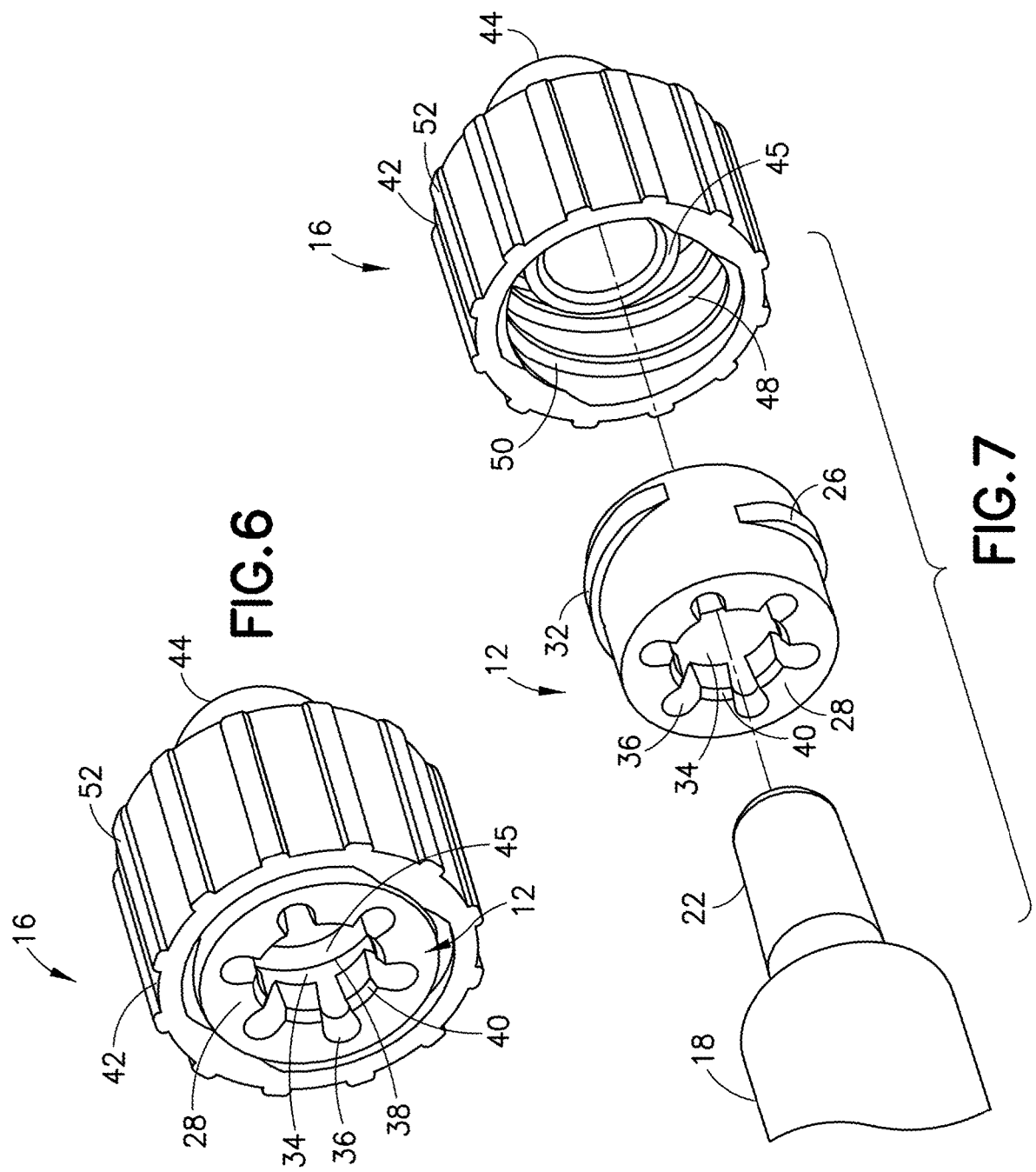

CAP HUB INTERFACE FOR INTRADERMAL INJECTION DEVICE

CROSS-REFERENCE TO RELATED APPLICATIONS

This application is the United States national phase of International Application No. PCT/IB2018/000675 filed Jun. 1, 2018, and claims priority to U.S. Provisional Patent Application No. 62/513,740 filed Jun. 1, 2017, the disclosures of which are hereby incorporated by reference in their entirety.

BACKGROUND OF THE INVENTION

Field of the Invention

The present disclosure, generally, is directed to a cap hub interface for an injection device and, in particular, to a cap hub interface for an intradermal injection device.

Description of Related Art

Currently, conventional luer lock syringes allow for connection of several different types and styles of needles. These different types of needles are used for a variety of applications, including intradermal needles, subcutaneous needles, intramuscular needles, and intravenous needles. Pharmaceutical companies have developed medicaments and drugs that are suitable for only one specific application (for example, only for an intradermal application). Local regulations in some regions of the world require the avoidance of any misconnection of a particular injection device with an undesired product or medicament. Therefore, there is a current need for an injection device configured to only receive a desired or predetermined syringe including a desired medicament or drug. Furthermore, there is a current need for an injection device configured to only connect to a predetermined or desired needle specific to the desired application.

SUMMARY OF THE INVENTION

In one example of the disclosure, an injection device including a syringe comprising a barrel having a distal end and a proximal end and a tip provided on the distal end of the barrel, the barrel defining an internal bore extending from the proximal end to the distal end of the barrel; a luer lock adaptor comprising a body having a proximal end and a distal end, a reduced-diameter portion provided on the proximal end of the body, and a threading provided on an outer surface of the body, the reduced-diameter portion defining an opening to receive the tip of the syringe in a friction fit; and a needle hub comprising a body defining an inner cavity, a needle receiving portion extending distally from the body, and a skirt extending inwardly into the inner cavity, wherein an inner surface of the body includes a threading corresponding to the threading of the luer lock adaptor to connect the luer lock adaptor to the needle hub, wherein the needle receiving portion defines a bore to receive the tip of the syringe.

In one configuration, the opening is sized to only accommodate the tip of the syringe, wherein the syringe is a predetermined syringe-type. The diameter of the opening may be smaller than an outer diameter of the tip of the syringe.

In certain configurations, the opening has a star-shaped configuration. In other configurations, the opening is discontinuous and includes a plurality of recesses that are formed with a central opening to form the opening. An edge of the opening may be chamfered.

The tip may include a groove therein and an edge of the opening may be chamfered to engage with the groove to hold the syringe within the luer lock adaptor. The bore defined by the needle receiving portion may have an inner surface which tapers from a distal end to a proximal end of the needle receiving portion. A diameter of the distal end of the bore may be greater than the diameter of the proximal end of the bore. In certain configurations, the diameter of the proximal end of the bore limits a distance between the distal end of the tip of the syringe and a distal end of the luer lock adaptor. The predetermined distance may be from between 2 and 2.5 mm.

In certain configurations, the body of the needle hub includes a plurality of gripping ribs defined in an outer surface of the body to assist a user in the holding of the needle hub during connection of the syringe into the luer lock adaptor and the needle hub.

These and other features and characteristics of the connecting arrangement, as well as the methods of operation and functions of the related elements of the arrangement, will become more apparent upon consideration of the following description with reference to the accompanying drawings, all of which form a part of this specification, wherein like reference numerals designate corresponding parts in the various figures. It is to be expressly understood, however, that the drawings are for the purposes of illustration and description only, and are not intended as a definition of the limits of the disclosure. As used in the specification, the singular form of "a", "an", and "the" include plural referents unless the context clearly dictates otherwise.

BRIEF DESCRIPTION OF THE DRAWINGS

FIG. 3 is a cross-sectional view of a distal end of the injection device of FIG. 1;

FIG. 4 is a cross-sectional view of another example of the injection device of the present disclosure;

FIG. 6 is a perspective view of a needle hub and luer lock adaptor according to one example of the present disclosure;

FIG. 7 is an exploded perspective view of the distal end of the injection device of FIG. 4;

DESCRIPTION OF THE DISCLOSURE

For purposes of the description hereinafter, the terms "upper", "lower", "right", "left", "vertical", "horizontal", "top", "bottom", "lateral", "longitudinal", and derivatives thereof, shall relate to the invention as it is oriented in the figures. However, it is to be understood that the invention may assume alternative variations and step sequences, except where expressly specified to the contrary. It is also to be understood that the specific systems and processes illustrated in the attached drawings, and described in the following specification, are simply exemplary examples of the invention. Hence, specific dimensions and other physical characteristics related to the examples disclosed herein are not to be considered as limiting.

Figure 1:
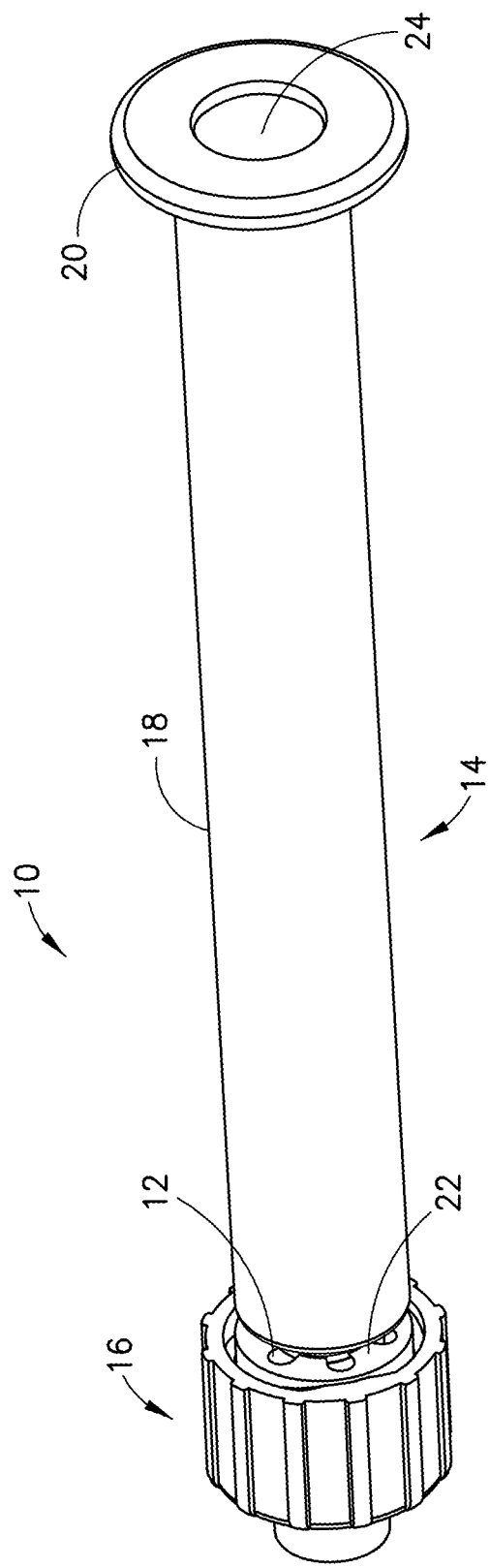
FIG. 1 is a perspective view of an injection device according to one example of the present disclosure.
Figure 2:
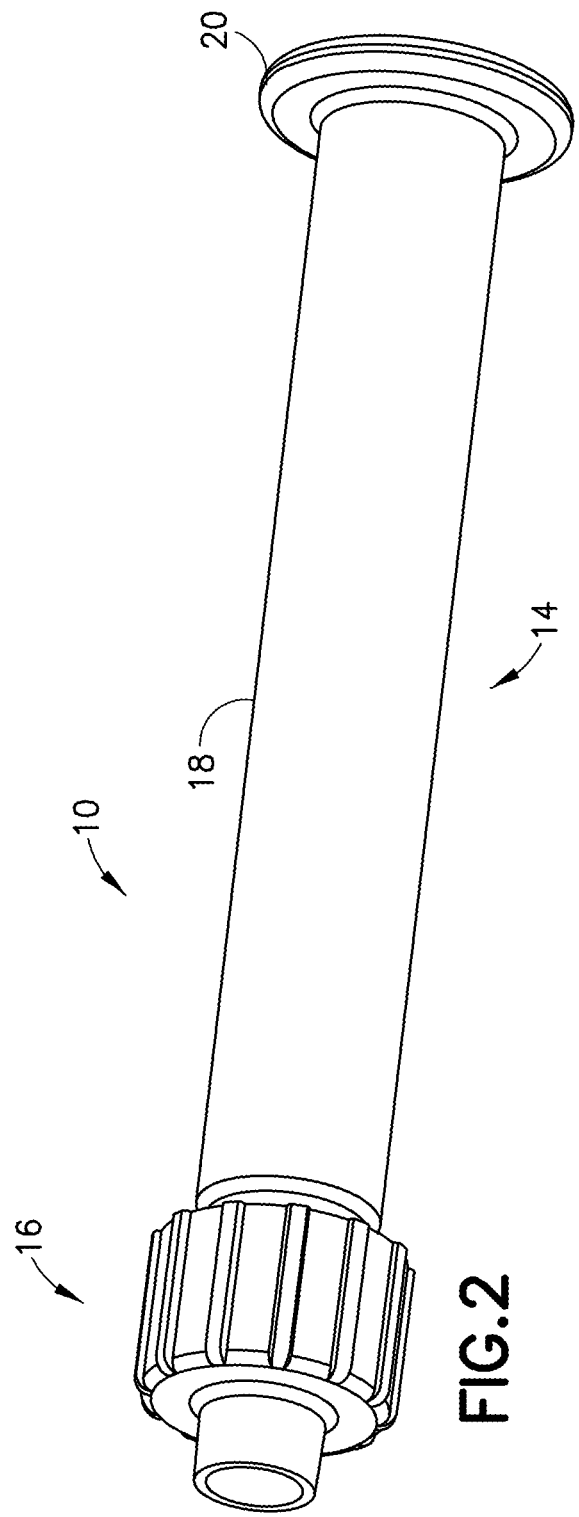
FIG. 2 is another perspective view of the injection device of FIG. 1.
Figure 5:
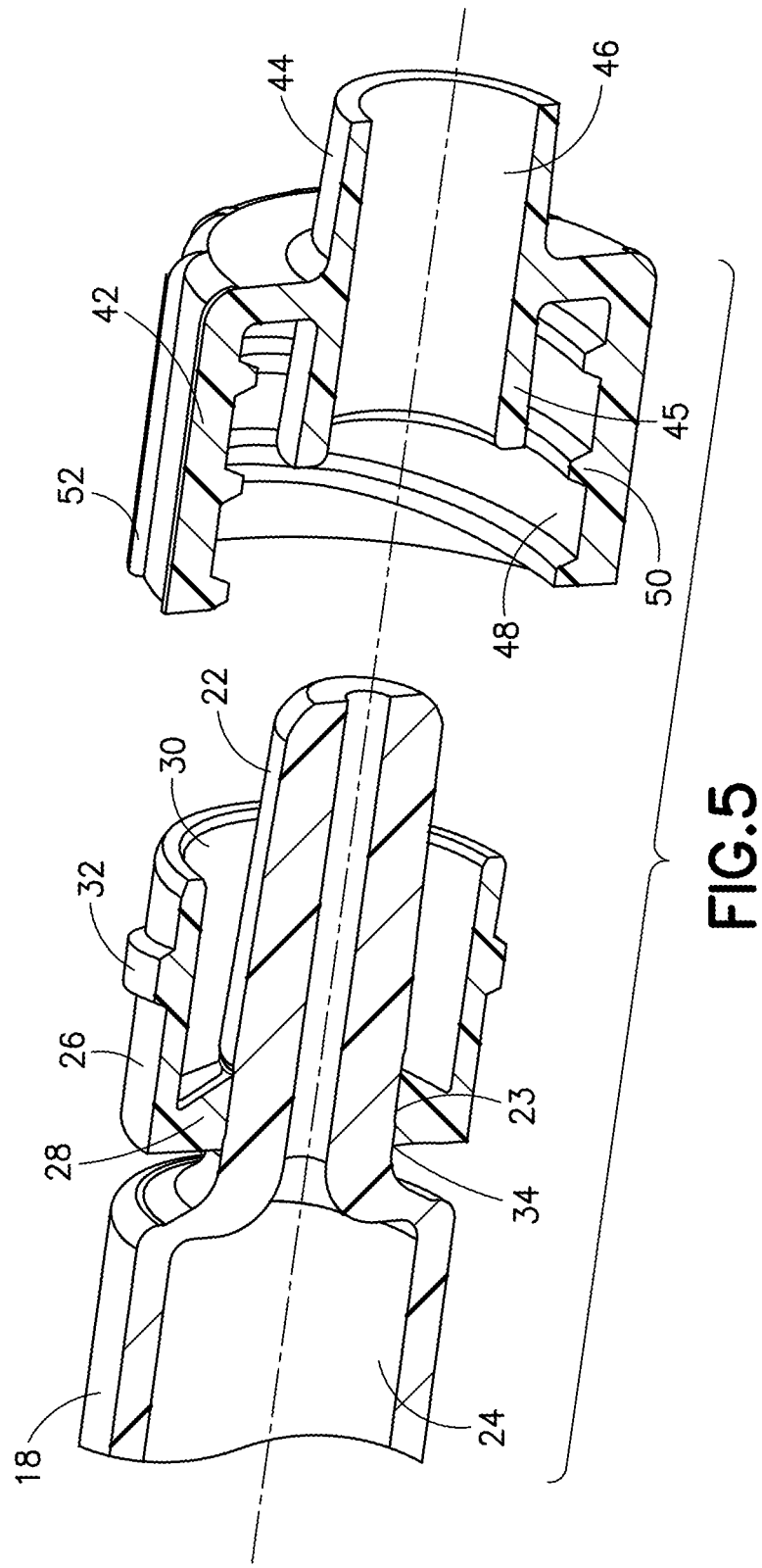
FIG. 5 is an exploded cross-sectional view of the distal end of the injection device of FIG. 4.
Figure 8:
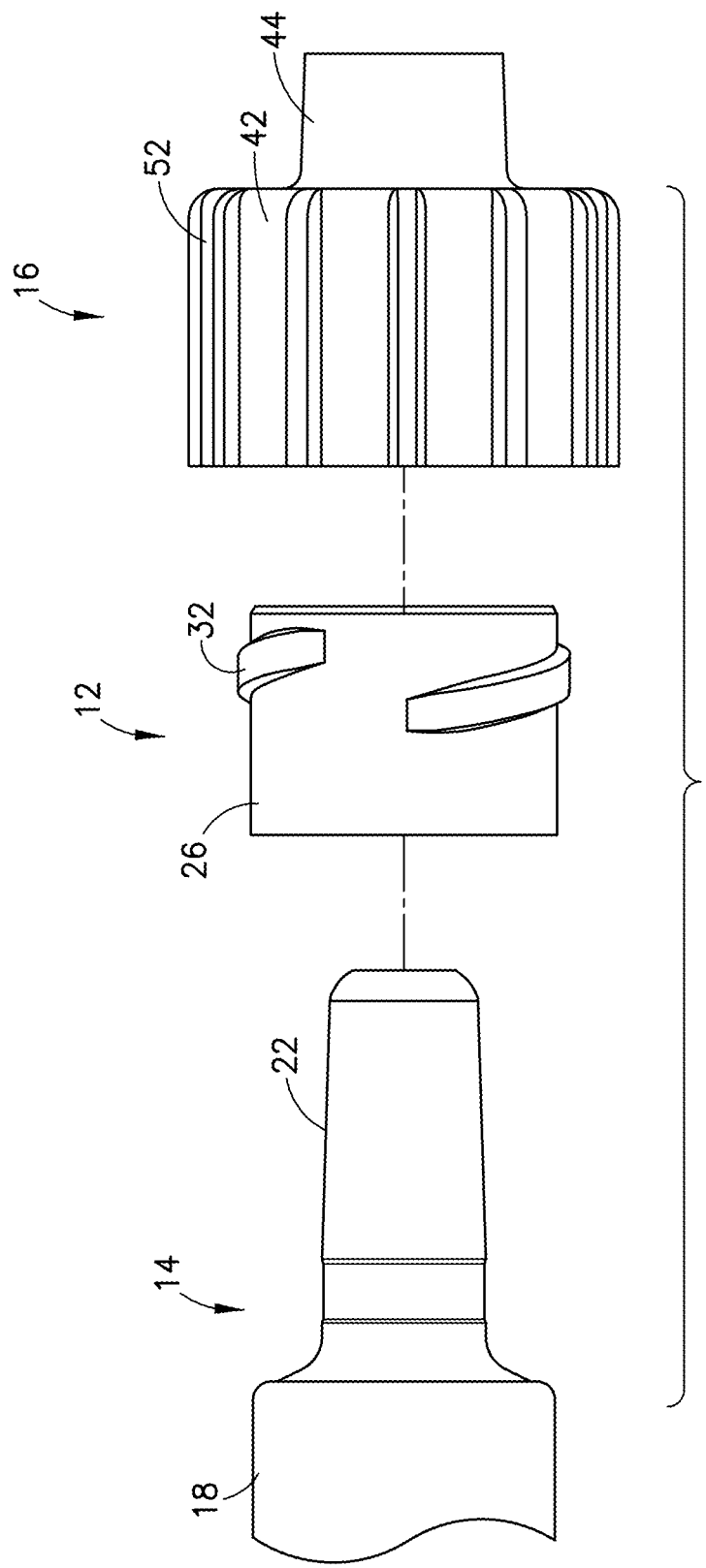
FIG. 8 is an exploded side view of the distal end of the injection device of FIG. 4.
Figure 9:
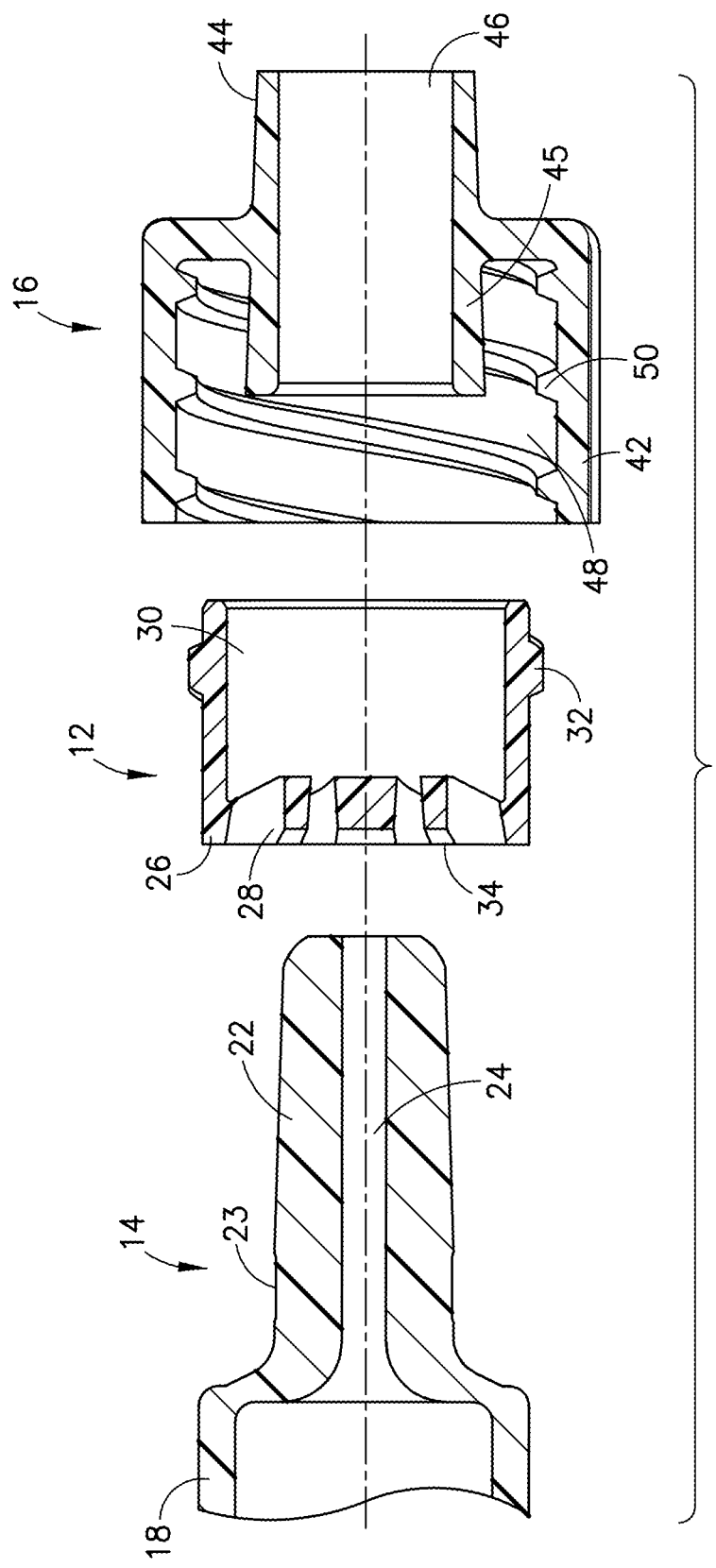
FIG. 9 is an exploded cross-sectional side view of the distal end of the injection device of FIG. 4.

The present disclosure, generally, is directed to an injection device 10 and, in particular, a luer lock adaptor 12 configured to assist in connecting a syringe 14 to a needle hub 16. The injection device 10 is described with reference to FIGS. 1-9.

With reference to FIGS. 1-9, the injection device 10 includes a syringe 14, a luer lock adaptor 12, and a needle hub 16. It is also contemplated that a removable gripping handle (not shown) may be provided on the syringe 14 to assist a user in holding or grasping the injection device 10. The syringe 14 includes a generally cylindrical syringe barrel 18, an integral flange 20 provided on a proximal end thereof, and a tip 22 provided on a distal end thereof. The tip 22 may have a smaller diameter than the syringe barrel 18. The tip 22 is configured for connection with a needle (not shown). In one example, as shown in FIG. 4, the tip 22 may define a groove 23 therein for assistance in connecting the syringe 14 to the luer lock adaptor 12, as explained in greater detail below. In one example, the syringe 14 may be made of glass. It is also contemplated that the syringe 14 may be made of transparent medical-grade plastic. The syringe 14 defines an internal bore 24 that extends from the proximal end to the distal end of the syringe 14. The internal bore 24 is configured to receive and hold a medicament to be injected into a patient.

As shown in FIGS. 3 and 4, in one example of the present disclosure, the luer lock adaptor 12 is threadedly connected to the needle hub 16 and friction fit on the tip 22 of the syringe 14. In one example, the luer lock adaptor 12 is made of a deformable plastic. The luer lock adaptor 12 includes a body member 26 and a reduced-diameter inner protrusion 28. The body member 26 defines an inner cavity 30 configured to receive a portion of the needle hub 16 and the tip 22 of the syringe 14. In one example, a diameter of the inner cavity 30 is generally 6.5-7 mm. The portion of the needle hub 16 is received in a distal end of the luer lock adaptor 12. The tip 22 of the syringe 14 is received within a proximal end of the luer lock adaptor 12. In one example, the body member 26 is generally cylindrical in shape. As shown in FIGS. 3 and 4, at least a portion of the outer circumferential surface of the body member 26 includes threading 32 to connect the luer lock adaptor 12 to the needle hub 16, as described in greater detail below. It is contemplated that the thread geometry of the threading 32, such as pitch and number of threads, can be adapted and modified as desired.

The inner protrusion 28 of the luer lock adaptor 12 defines an opening 34 in the proximal end of the luer lock adaptor 12. The opening 34 is configured to receive the tip 22 of the syringe 14. It is contemplated that the diameter of the opening 34 can be modified or adapted to accommodate different size syringe tips. The opening 34 is sized such that only a desired or predetermined syringe 14 can be received within the luer lock adaptor 12, thereby avoiding misconnection of an undesired syringe 14 within the injection device 10. In one example, the diameter of the opening 34 is slightly less than an outer diameter of the tip 22 of the syringe 14 so that the tip 22 is held by a friction fit within the opening 34. It is also contemplated that a snap-fit connection, an interference fit connection, an adhesive, or any other connection method could be used to hold the tip 22 within the opening 34. As shown in FIG. 6, the opening 34 may have a star-shaped configuration. The opening 34 may be discontinuous and include several different recesses 36 that are formed with a central opening 38 to form the overall opening 34. Certain edges 40 of the opening 34 may be chamfered to assist in the insertion of the syringe tip 22 into the luer lock adaptor 12. With reference to FIG. 4, in the embodiment of the injection device 10 in which a groove 23 is defined on the tip 22 of the syringe 14, as the syringe tip 22 is inserted into the luer lock adaptor 12, the edges 40 engage with the groove 23 defined on the syringe tip 22 to hold the syringe 14 within the luer lock adaptor 12.

With reference to FIGS. 1-4, the needle hub 16 has a generally cylindrical body 42, a needle receiving portion 44, and an inner skirt member 45. The needle receiving portion 44 is provided on a distal end of the body 42 and has a smaller diameter than the body 42. The needle receiving portion 44 defines a bore 46 adapted to receive a needle (not shown) for connection to the tip 22 of the syringe 14. The inner surface of the bore 46 tapers from a distal end to a proximal end of the needle receiving portion 44. Therefore, the diameter of the distal end of the bore 46 is greater than the diameter of the proximal end of the bore 46. Due to the reduced diameter of the proximal end of the bore 46, the tip 22 of the syringe 14 is held in a friction fit with the needle hub 16. In one example, the diameter of the proximal end of the bore 46 is designed such that a predetermined distance A between a distal end of the tip 22 and a distal end of the luer lock adaptor 12 is maintained. In one example, the distance A is measured to be generally between 2 and 2.5 mm. This distance is maintained to ensure that only a particular predetermined needle (not shown) can be received within the bore 46 of the luer lock adaptor 16. In the event this distance is too great, the desired needle may not be able to reach the tip 22 of the syringe 14 for connection thereto. In the event this distance is too small, other needles besides the particular predetermined needle may be received within the bore 46. By providing a specific interface between the needle hub 16 and the luer lock adaptor 12, the predetermined distance A can be maintained such that only one needle, one type of needle, or one length of needle may be fitted to the injection device 10. For example, by providing a specific interface between the needle hub 16 and the luer lock adaptor 12, only an intradermal needle could be fitted to the injection device 10, and not a subcutaneous, intramuscular, or intravenous needle.

The body 42 of the needle hub 16 defines an inner cavity 48 that receives the luer lock adaptor 12 and the tip 22 of the syringe 14. An inner surface of the body 42 includes a threading 50 that corresponds to the threading 32 of the luer lock adaptor 12. It is contemplated that the thread geometry of the threading 50, such as pitch and number of threads, can be adapted and modified as desired. The luer lock adaptor 12 may be threaded into the inner cavity 48 of the needle hub 16 by connecting the corresponding threading 32, 50 with one another. This threaded connection prevents the luer lock adaptor 12 from moving proximally out of the needle hub 16. The body 42 may also define a plurality of gripping ribs 52 in an outer circumferential surface of the body 42. The ribs 52 assist a user in holding and gripping the needle hub 16 during connection of the syringe 14 into the luer lock adaptor 12 and the needle hub 14.

While several examples of the injection device are shown in the accompanying figures and described in detail hereinabove, other aspects will be apparent to, and readily made by, those skilled in the art without departing from the scope and spirit of the disclosure. Accordingly, the foregoing description is intended to be illustrative rather than restrictive.

The invention claimed is:

1. An injection device, comprising:
   a syringe comprising a barrel having a distal end and a proximal end and a tip provided on the distal end of the barrel, the barrel defining an internal bore extending from the proximal end to the distal end of the barrel;
   a luer lock adaptor comprising a body having a proximal end and a distal end, a reduced-diameter portion provided on the proximal end of the body, and a threading provided on an outer surface of the body, the reduced-diameter portion defining an opening to receive the tip of the syringe in a friction fit; and
   a needle hub comprising a body defining an inner cavity, a needle receiving portion extending distally from the body, and a skirt extending inwardly into the inner cavity, wherein an inner surface of the body includes a threading corresponding to the threading of the luer lock adaptor to connect the luer lock adaptor to the needle hub, wherein the needle receiving portion defines a bore to receive the tip of the syringe.

2. The injection device of claim 1, wherein the opening is sized to only accommodate the tip of the syringe, wherein the syringe is a predetermined syringe-type.

3. The injection device of claim 1, wherein the diameter of the opening is smaller than an outer diameter of the tip of the syringe.

4. The injection device of claim 1, wherein the opening has a star-shaped configuration.

5. The injection device of claim 1, wherein the opening is discontinuous and includes a plurality of recesses that are formed with a central opening to form the opening.

6. The injection device of claim 1, wherein an edge of the opening is chamfered.

7. The injection device of claim 1, wherein the tip includes a groove therein and an edge of the opening is chamfered to engage with the groove to hold the syringe within the luer lock adaptor.

8. The injection device of claim 1, wherein the bore defined by the needle receiving portion has an inner surface which tapers from a distal end to a proximal end of the needle receiving portion.

9. The injection device of claim 8, wherein a diameter of the distal end of the bore is greater than the diameter of the proximal end of the bore.

10. The injection device of claim 9, wherein the diameter of the proximal end of the bore limits a distance between the distal end of the tip of the syringe and a distal end of the luer lock adaptor.

11. The injection device of claim 10, wherein the predetermined distance is from between 2 and 2.5 mm.

12. The injection device of claim 1, wherein the body of the needle hub includes a plurality of gripping ribs defined in an outer surface of the body to assist a user in the holding of the needle hub during connection of the syringe into the luer lock adaptor and the needle hub.

* * * * *